United States Patent [19]
Fernald

[11] Patent Number: 5,626,625
[45] Date of Patent: May 6, 1997

[54] METHOD AND APPARATUS FOR MEASURING THE PERIOD OF RESPONSE OF AN IMPLANTABLE MEDICAL DEVICE BASED UPON THE DIFFERENCE IN PHASE BETWEEN A TRIGGER SIGNAL AND AN INTERNAL CLOCK SIGNAL

[75] Inventor: Kenneth W. Fernald, Lake Jackson, Tex.

[73] Assignee: Intermedics, Inc., Angleton, Tex.

[21] Appl. No.: 591,317

[22] Filed: Jan. 25, 1996

Related U.S. Application Data

[62] Division of Ser. No. 333,163, Nov. 1, 1994, Pat. No. 5,522,866.

[51] Int. Cl.$^6$ .................... A61N 1/08; A61N 1/02
[52] U.S. Cl. .................... 607/32; 607/60; 128/903
[58] Field of Search ................ 607/32, 60; 128/903

[56] References Cited

U.S. PATENT DOCUMENTS

| | | | |
|---|---|---|---|
| 5,034,967 | 7/1991 | Cox et al. | 375/119 |
| 5,137,022 | 8/1992 | Henry | 607/32 |
| 5,241,961 | 9/1993 | Henry | 128/903 |
| 5,294,842 | 3/1994 | Iknaian et al. | 307/269 |
| 5,315,183 | 5/1994 | Ruotsalainen | 307/511 |
| 5,411,536 | 5/1995 | Armstrong | 607/32 |
| 5,480,415 | 1/1996 | Cox et al. | 607/32 |

*Primary Examiner*—William E. Kamm
*Assistant Examiner*—Carl H. Layno
*Attorney, Agent, or Firm*—Michael F. Heim, Conley, Rose & Tayon, PC

[57] ABSTRACT

A method and apparatus is disclosed for use in an implantable device that communicates with an external device through pulse position modulation. A timing generator is provided as part of the implantable device that determines the phase uncertainty between an external signal and an internal cock signal. The phase uncertainty then is added to the preset delay period to more precisely control the position of the response. The phase uncertainty is measured by a dual slope circuit that varies a state variable (which can be a digital timer, a capacitor voltage, or the like) at a fixed rate with either a positive or negative slope. When the external signal is detected, the stat variable is reset and then decreased at a fixed rate until the next positive edge of the clock signal. The state variable then is increased at the same rate until the subsequent positive clock edge. The resulting variable value is proportional to the phase uncertainty. When the delay timer reaches zero, the state variable is again decreased at the same fixed rate until the initial value is reached, at which the output response is generated.

17 Claims, 7 Drawing Sheets

METHOD AND APPARATUS FOR MEASURING THE PERIOD OF RESPONSE OF AN IMPLANTABLE MEDICAL DEVICE BASED UPON THE DIFFERENCE IN PHASE BETWEEN A TRIGGER SIGNAL AND AN INTERNAL CLOCK SIGNAL

This application is a divisional application of U.S. Ser. No. 08/333,163, filed Nov. 1, 1994 and issued as U.S. Pat. No. 5,522,866 on Jun. 4, 1996.

BACKGROUND OF THE INVENTION

The present invention relates generally to an implantable medical device capable of communicating with an external device. More particularly, the invention relates to a programmable implantable device that transmits and receives data from an external device via pulse position modulation, and which includes a timing generator to measure the proper delay period for responding to a trigger signal received from an external device. Still more particularly, the present invention relates to a phase measurement technique implemented in a programmable implantable device for synchronizing an asynchronous input signal from an external device to increase the resolution and throughput of the data transfer.

Disruption of natural pacemaking capabilities in the heart as a result of aging or disease is commonly treated by the insertion into a patient of an artificial cardiac pacing device, commonly referred to as a pacemaker. A pacemaker provides rhythmic electrical discharges that are applied to the heart at a desired rate from the implanted artificial pacemaker. In its simplest form, the pacemaker consists of a pulse generator powered by a self-contained battery pack, and a lead including at least one stimulating electrode(s) for delivery of electrical impulses to excitable myocardial tissue in the appropriate chamber(s) in the right side of the patient's heart. However, in some instances epicardial electrodes are implanted by surgically splitting the patient's chest or other well known techniques, and suturing or screwing them in to the epicardium. Typically, the pulse generator is surgically implanted in a subcutaneous pouch in the patient's chest. In operation, the electrical stimuli are delivered to the excitable cardiac tissue via an electrical circuit that includes the stimulating and reference electrodes, and the body tissue and fluids.

Pacemakers range from the simple fixed rate device that provides pacing with no sensing function, to highly complex models implemented to provide fully automatic dual chamber pacing and sensing functions. The latter type of pacemaker is the latest in a progression toward physiologic pacing, that is, the mode of artificial pacing that restores cardiac function as much as possible toward natural pacing.

Historically, pacemakers have been employed primarily for the treatment of bradyarrhythmias, but over the past several years cardiac pacing has found significantly increasing usage in the management of tachyarrhythmias. Antitachyrhythmia pacemakers take advantage of an inhibitory mechanism that acts on the secondary natural pacemakers to prevent their spontaneous automaticity, sometimes termed "postdrive inhibition" or "overdrive inhibition." In essence, the heart may be driven (stimulated) with faster than normal pacing rate to suppress ectopic activity in the form of premature atrial or ventricular contractions (extrasystoles) that might otherwise initiate supraventricular or ventricular tachycardia, flutter (typically, a tachyrhythmia exceeding 200 bpm), Or fibrillation; or to terminate an existing tachyrhythmia.

The pulses delivered to the heart for pacing therapy need only be of sufficient magnitude to stimulate the excitable myocardial tissue in the immediate vicinity of the pacing electrode. In contrast, another technique for terminating tachycardias, termed cardioversion, utilizes apparatus to shock the heart with one or more current or voltage pulses of generally considerably higher energy content than is delivered in pacing pulses. Whether pacing or cardioverting therapy is employed in an effort to terminate a tachycardia, a considerable risk is present that the treatment itself may precipitate fibrillation.

Defibrillation ("DF"), the method employed to terminate fibrillation, involves applying one or more high energy "countershocks" to the heart in an effort to overwhelm the chaotic contractions of individual tissue sections, allow reestablishment of an organized spreading of action potential from cell to cell of the myocardium, and thus restore the synchronized contraction of the mass of tissue.

Typically, and as shown in FIG. 1, an implantable medical device 12, such as a pacemaker, for example, comprises electrical circuits that are controlled by processing circuitry 26, such as a central processing unit (CPU) or microprocessor. Because of the implementation of the microprocessor in the pacemaker or other implantable device, the pacemaker can be programmed by a physician through an external device 10 to customize the operation of the device to the patient's conditions. As shown in FIG. 1, the pacemaker or other implantable device 12 includes a coil antenna 30 which is capable of communicating through electromagnetic waves to a coil antenna 24 in the external programmer/reader 20 in the external device 10. The pacemaker can be programmed after it is implanted in the patient 14 through electromagnetic signals transmitted by the external programmer. The pacemaker 12 attaches to the patient's heart 16 through electrical leads 18. The pacemaker also includes a communications interface 28 to transmit and receive signals through an antenna 30. Similarly, the external device 10 also includes a communications interface 22 connected to antenna 24.

In addition to the microprocessor, the pacemaker also may include a memory device (not shown), such as random access memory (RAM) chips, for storing signals indicative of the patient's health. The pacemaker may have the capability of monitoring physiological parameters of the patient, such as EKG signals, and may store digital signals representative of these parameters in the memory device. When prompted by the external device, the processing circuitry 26 can transmit the contents of the memory device to the external programmer/reader 20 for analysis by the physician.

Because of the large amount of data that may be transmitted between the pacemaker and the external device, a significant amount of time may be required to complete the data communications. The data transactions could be expedited by the use of higher speed electronics, but the use of such high speed circuitry requires large power supplies. A pacemaker includes a battery (not shown) for operating the circuitry, which preferably has a life of 5–10 years. Operating the pacemaker circuitry at higher frequencies results in greater power consumption, which could greatly curtail the life of the battery, requiting surgery to replace. Power consumption, therefore, is at a premium in such an implantable device.

In commonly assigned U.S. Pat. No. 5,383,912, entitled "Apparatus and Method for High Speed Data Communication Between an External Medical Device and an Implantable Medical Device," the teachings of which are incorporated by reference herein, the assignee of the present invention has developed a pacemaker, capable of high speed data communication, which uses energy from the signal transmitted by the external device to generate a pulse position modulated response.

Data is transferred in commonly assigned, U.S. Pat. No. 5,383,912 through the use of pulse position modulation. A trigger signal is transmitted by the external device 10, and the processing circuitry 26 in the pacemaker responds with n output signal that is transmitted to the external device after a certain delay period. The period of delay defines the response. This is done by allocating certain window periods for a response, so that the time period during which that response occurs determines the data to be conveyed. For example, after the trigger signal is received from the external device, the system might allocate sixteen window periods for a response to represent the transfer of four digital bits ($2^4=16$). The time during which the response is sent indicates the digital data being transferred. Thus, if the response fell in the ninth available window period, a digital 9, or 1001, might be indicated. Subsequent data transfers occur in similar fashion until all data has been transferred. This procedure is implemented by including a digital counter or timing generator in the implantable device. The digital timing generator is initialized on the first rising clock edge following receipt of the trigger signal. The desired delay is loaded into the digital counter, so that when the count reaches zero, an output signal is generated to the external device.

One potential shortcoming with this arrangement is the asynchronism between the external trigger signal and the internal clock signal of the implantable device. As a result, the window periods for the pulse position modulated response cannot be finely resolved. Instead, the window periods must be defined sufficiently broadly to account for delays in detecting the asynchronous trigger signal. This is necessary because the trigger signal is not synchronized with the internal system clock signal which initiates the timing generator, and thus the digital timing generator may not begin counting until a full clock cycle after the trigger signal is transmitted.

The telemetering circuitry in the pacemaker sets the delay counter for the window periods immediately upon receiving the trigger signal. The delay counter, however, does not begin counting until the subsequent rising clock edge, thereby creating a potential delay between transmission of the trigger signal and the start of the digital delay counter. As a result, the timing generator potentially does not begin until almost a full clock signal after the trigger signal. A timing diagram for a digital delay counter is shown in FIG. 2. When designing a delay counter, the possibility of the trigger occurring asynchronously relative to the internal clock must be considered. The internal clock signal drives the countdown digital timing generator on a clock edge in accordance with conventional techniques. At the clock edge (which for example may be a rising clock edge) following the occurrence of the trigger signal, the digital timing generator begins counting down the preset delay value (expressed as a multiple of the clock period). The output response is then generated when the timing generator value reaches 0, as shown in FIG. 2. Because the input trigger can occur at any point within a particular clock period, the actual delay $T_a$ is given by:

$$T_A = \text{PRESET} \times T_{CLK} - T_E$$

where PRESET is the timer preset value, $T_{CLK}$ is the internal clock period, and $T_E$ is the phase uncertainty between the clock signal and the input event. The value of $T_E$, which represents the error between the actual delay achieved and the desired delay, can vary from 0 to $T_{CLK}$. Depending on the specifics of the system design, this uncertainty may exceed the required error tolerance, and hence destroy the information integrity.

One way to increase the resolution of the transmission is simply to provide a faster internal clock to minimize the possible phase uncertainty between the internal clock and the trigger input. Unfortunately, this higher clock frequency results in proportionally higher power consumption by the oscillator driving the internal clock and the digital circuitry used in the implantable device. In addition, many digital systems may not be operable at a higher clock frequency due to frequency dependencies already incorporated into their designs.

It would be advantageous, therefore, to develop a system for detecting phase uncertainty between an internal clock and a trigger event to increase the resolution and bandwidth of the data transfer.

SUMMARY OF THE INVENTION

The present invention solves the shortcomings and deficiencies of the prior art by constructing an implantable device with a dual slope circuit to measure the phase uncertainty between the internal clock and the trigger event. The measured phase uncertainty then is added to the desired delay to correct automatically for phase uncertainty.

The present invention can be implemented in a circuit that is capable of varying a state variable at a fixed rate with either a positive or negative slope. When the input trigger is detected, the state variable is reset to a known value, then decreased at a fixed rate (M) until the next positive-edge of the internal clock signal. The state variable then is increased at the same rate until the next positive clock edge. The resulting variable value then is proportional to the phase uncertainty $T_E$. When the digital counter reaches 0, the state variable is again decreased at the same rate (M) until it reaches the initial value, which indicates it is time to generate an output response. The resulting delay achieved $T_A$ will then equal the desired delay regardless of the phase uncertainty between the trigger and clock signals.

The timing generator may be implemented with either digital or analog circuitry. In the digital implementation, a fast relaxation oscillator is used as an input clocking signal to a phase timer. The direction in which the phase timer counts is determined by a logic circuit comprised of a pair of D flip-flops. The fast oscillator controls the rate at which the phase timer counts, and only is used when the trigger signal is detected to save power. Conversely, in the analog implementation, a capacitor is used as the phase timer with a pair of current sources to control the rate of change of the voltage on the capacitor.

Other methods also can be employed to measure the phase uncertainty using similar techniques. For example, both edges of the clock signal may be used to measure the phase uncertainty. After the trigger event is received, the timing generator may count down at a fixed rate until the next clock edge occurs, at which time the timing generator counts up at the same fixed rate. At the subsequent clock edge the state variable in the timing generator remains fixed until the delay timer has expired, after which the timing generator counts down from the fixed state variable value at the fixed rate. When the timing generator count goes to zero, the output is enabled from the implantable device.

The present invention also has application outside of pulse position modulation. For example, the above techniques may be used to synchronize an internal clock to an asynchronous event, or can even be used to measure the time between two asynchronous events.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

Figure 2:
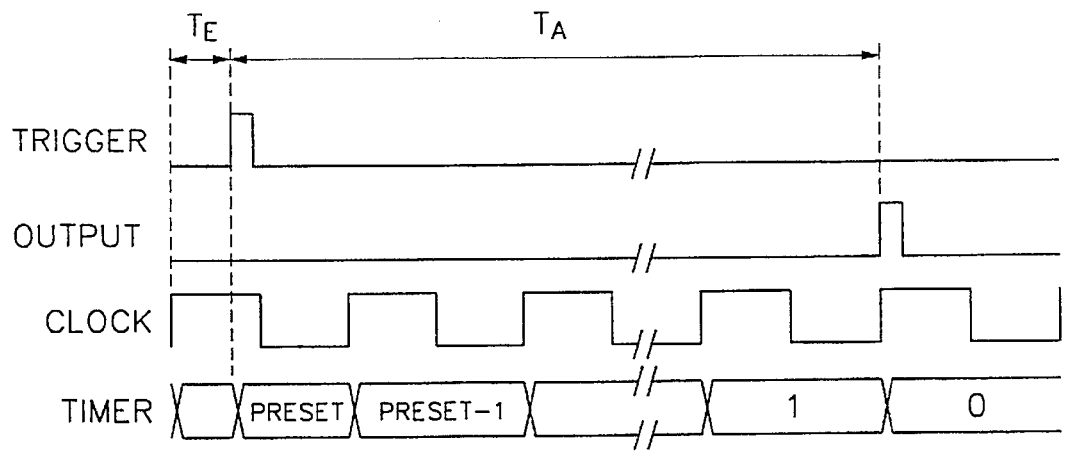
FIG. 2 depicts a timing diagram illustrating the potential phase uncertainty which may result from using a conventional digital timing generator to produce an output in response to an asynchronous event.

The present invention is designed specifically for an implantable medical device which communicates with an external device by pulse position modulation. Pulse position modulation is described in the Background of the Invention with respect to FIG. 2.

Figure 1:
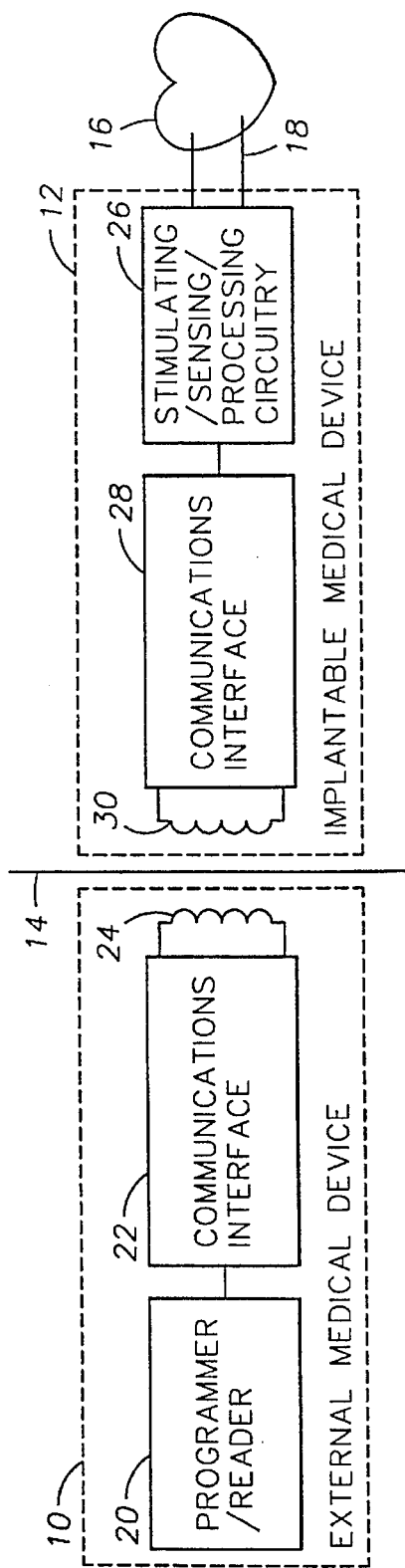
FIG. 1 is a functional block diagram illustrating the manner in which an implantable medical device communicates with an external device.
Figure 1A:
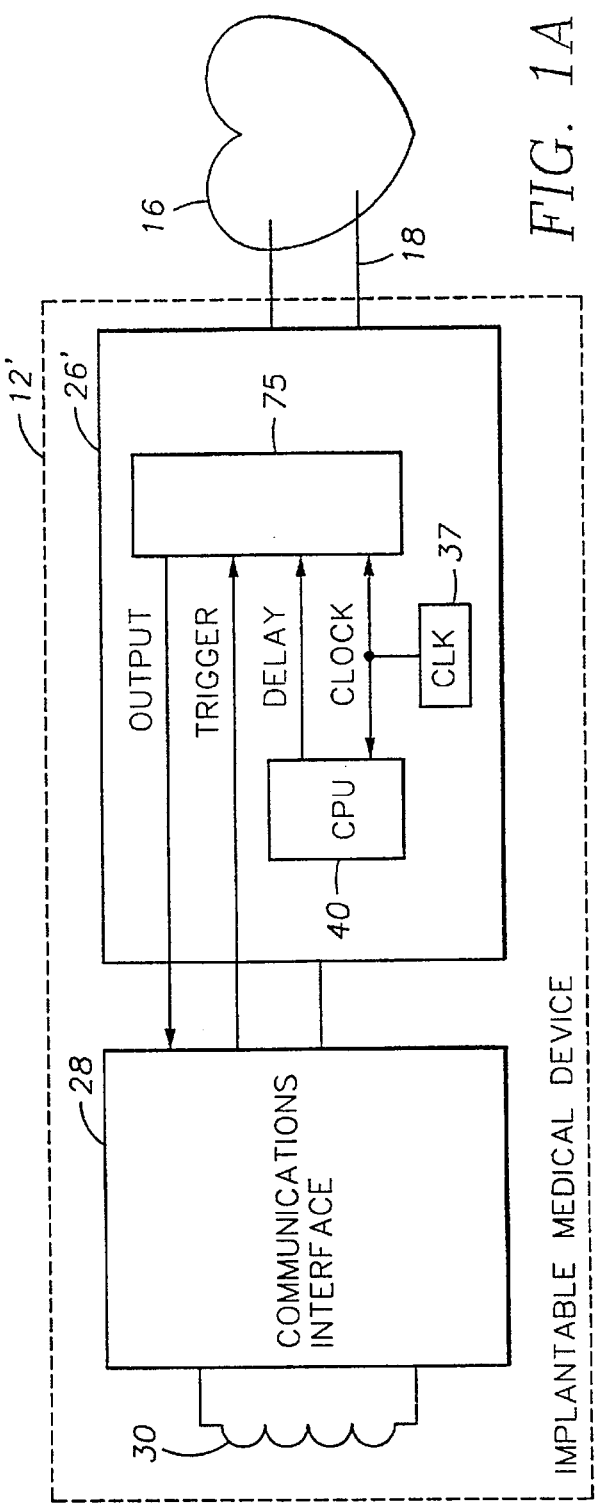
FIG. 1A is a functional block diagram of an implantable device constructed in accordance with the preferred embodiment.

In the preferred embodiment shown in FIG. 1A, the implantable medical device 12' generally comprises processing circuitry 26' which includes a CPU 40, an internal clock 37, and a timing generator 75, which causes the implantable device 12' to respond to a trigger (TRIGGER) signal after a preset delay period. The implantable medical device, which in the preferred embodiment is a pacemaker, also includes a communications interface 28, an antenna 30, and leads 18 connecting the device 12' to a patient's heart..One skilled in the art will understand, however, that the present invention may be used with any implantable device, or in other telemetering situations in which a trigger event occurs asynchronously with a system clock.

As shown in the preferred embodiment of FIG. 1A, the processing circuitry 26' of the pacemaker 12' receives as an input a TRIGGER signal, which is received via antenna 30 from an external device. In response, and after a preset time delay, which is shown as the DELAY signal from CPU 40, the timing generator 75 produces an OUTPUT signal that is transmitted via antenna 30 to an external device. An internal clock 37, such as a crystal oscillator, provides an internal clock (CLOCK) signal to the processing circuitry 26' components. Typical frequencies for the internal clock are 100–200 kHz.

Figure 3:
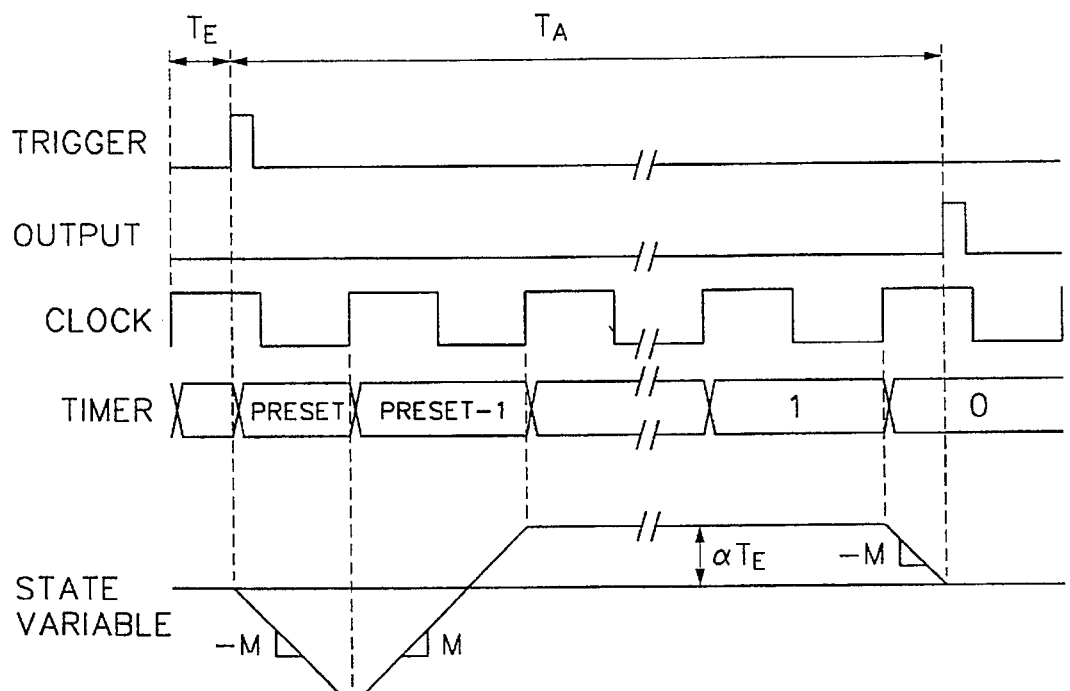
FIG. 3 is a timing diagram illustrating the methodology employed in the preferred embodiment.

Referring now to FIG. 3, the methodology employed in the preferred embodiment of the present invention comprises a technique for automatically measuring phase uncertainty, and adding to the preset delay period an additional delay period representing the phase uncertainty between the trigger event or TRIGGER signal and the internal CLOCK signal. The present invention preferably includes a dual-slope circuit, which is discussed in more detail below, to measure the period (or phase uncertainty) between the rising edge of the clock signal and the trigger event. The measured phase uncertainty then is added to the preset delay period from the digital delay timer, thereby correcting automatically for phase uncertainty.

One manner of performing this method is shown in FIG. 3. As shown in FIG. 3, a system clock is provided which provides a clock frequency $f_{CLK}$ (with a period of $t_{CLK}$) to the pacemaker circuitry at a preselected frequency. In the preferred embodiment, the digital circuitry in the pacemaker performs operations on the rising edge of the clock signal. A trigger event may occur sometime after the rising edge of a clock signal (this delay period is represented as $T_E$). As one skilled in the art will understand, the pacemaker circuitry will not respond to the trigger event until the subsequent rising clock edge, thereby introducing a phase uncertainty $(T_E)$ of $0<T_E<t_{ax}$. The phase uncertainty $(T_E)$ is represented in FIG. 3 as the distance from the previous rising clock edge to the trigger signal. At the subsequent clock edge (following the PRESET period), the digital timer or counter begins counting down the preset value for the pulse position modulated response. At each subsequent rising clock edge, the digital timer is decremented.

The present invention also includes a circuit which varies a state variable, which can comprise either a digital timer or a capacitor voltage, at a fixed rate with either a positive or negative slope. When the input trigger is detected, the state variable is reset to a known value (such as zero in the preferred embodiment), then decreased at a fixed rate (M) until the next positive clock edge occurs. The state variable then is preferably increased at the same rate (M) until the subsequent clock edge. The resulting variable value is proportional to the phase uncertainty $T_E$. When the delay timer or counter reaches zero, the state variable again is decreased at the same rate (M) until the state variable reaches its initial value, at which time the pacemaker is enabled to issue its pulse position modulated response. The resulting delay $T_A$ of the modulated response will equal the preset delay regardless of the phase uncertainty $T_E$ between the trigger and the clock signal.

The above method has several advantages when compared to alternative methods. First, it allows the digital delay timer or counter to operate from a standard crystal oscillator, which provides excellent long-term accuracy at a reasonable cost. In addition, because the crystal oscillator is allowed to run freely, it can also be used by other digital circuitry in the pacemaker, resulting in potential power savings. Moreover, because the same circuit is used to both decrease and increase the state variable, the exact rate of change (or slope) of the variable is irrelevant, as long as the rate is constant. Consequently, the system is relatively immune to parasitic effects, and eliminates the necessity of high precision components.

Figure 6:
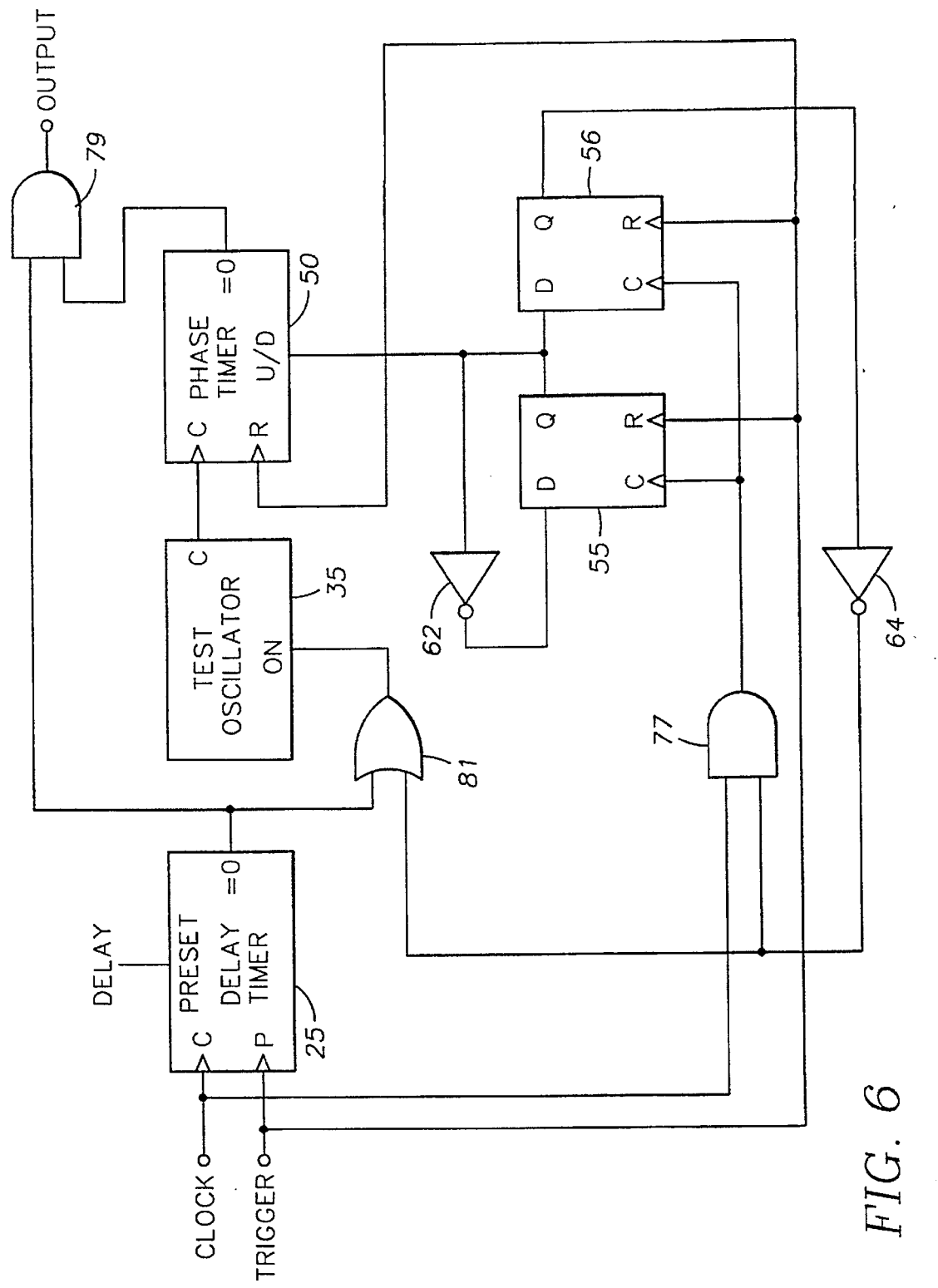
FIG. 6 is a schematic drawing depicting the preferred construction of a timing generator in accordance with the method of FIG. 3.

Referring now to FIGS. 1A and 6, timing generator 75 preferably is constructed to operate in accordance with the methodology of FIG. 3. The timing generator 75 of FIG. 6 preferably is constructed entirely of digital logic, and includes a delay timer 25, a fast or high 18 speed oscillator 35, a phase timer 50, and first and second D flip-flops 55, 56. The timing generator 75 receives as input signals a clock signal (CLOCK) which is the internal clock signal for the device 12, a trigger input (TRIGGER) from the communications interface 28, and a delay (DELAY) signal which is received from the CPU 30 to set the PRESET period. The timing generator 75 produces an OUTPUT signal, which is provided to communications interface 28 to generate an output signal to the external device 10.

Referring still to FIG. 6, the CLOCK signal is provided as an input to the delay timer 25 and as one input to an AND gate 77. The CLOCK signal typically has a frequency in the range of 100–200 kHz. The output of AND gate 77 connects as the clock input to flip-flops 55, 56. The TRIGGER input is provided as an input to the delay timer 25, as a reset input to the flip-flops 55, 56, and as a reset input to the phase timer 50. The DELAY signal is provided as a preset signal to the delay timer 25.

The output of the delay timer 25 connects as one input of an OR gate 81, which in turn connects to the on gate of the fast oscillator 35. The speed of the fast oscillator need only be fast enough to provide additional resolution to the system clock signal. A 1 MHz oscillator, for example, would provide sufficient resolution for a system clock of 100–200 kHz. Because the fast oscillator only operates when a trigger signal is detected, the speed of this oscillator does not consume a significant amount of power. The fast oscillator 35 preferably comprises a relaxation oscillator which turns on without any significant start-up time.

The output of timer 25 also connects as one input to AND gate 79, which generates the OUTPUT signal for timing generator 75. The fast oscillator 35 produces a clock signal that clocks the phase timer 50. The phase timer 50 includes an up/down input which connects to the Q output of flip-flop 55. The value in phase timer 50 preferably represents the value of the state variable in FIG. 3. The Q output of flip-flop 55 also is provided as the data input of flip-flop 56, and is fed back through invertor 62 to the input of flip-flop 55. The Q output of flip-flop 56 is provided through invertor 64 as the second input to AND gate 77, and as the second input to OR gate 81.

In operation, a positive edge on the TRIGGER input causes the delay timer 25 to preset with the value on the DELAY input, and also resets flip-flops 55, 56 and phase timer 50. The low Q output of flip-flop 55 is provided as the up/down input to the phase timer 50, causing the timer 50 to count down. When flip-flop 56 is reset, the Q output of flip-flop 56 goes low. The Q output is inverted by invertor 64 and provided as an input to OR gate 81, turning on the fast oscillator 35. The fast oscillator 35 provides a clock signal to the phase timer 50, causing the timer 50 to count down at a fixed rate in accordance with FIG. 3.

On the subsequent rising clock edge of the CLOCK signal, the delay timer 25 begins counting down to zero. The rising edge CLOCK signal also is provided as a second input to AND gate 77, producing a high output signal to the clock input of flip-flops 55, 56, causing these flip-flops to transfer the signal at its data (D) input to its Q output. As a result, a high output appears at the Q output of flip-flop 55, and a low remains at the Q output of flip-flop 56. The high output of flip-flop 55 causes the phase timer 50 to count up at the fixed rate determined by the fast oscillator, and as shown in FIG. 3.

On the subsequent rising edge of the CLOCK signal, the Q output of flip-flop 55 goes low. Substantially concurrently, the Q output of flip-flop 56 goes high, producing a low signal at the input of AND gate 77 and of OR gate 81, thus turning off the CLOCK input to flip-flops 55, 56, and turning off fast oscillator 35. As a result, the value in phase timer 50 is held fixed. This value is proportional to the phase delay $T_E$. On each subsequent rising edge CLOCK signal, the delay timer 25 performs another count until it reaches zero.

When the delay timer 25 reaches zero, the delay timer 25 produces a high output signal to OR gate 81 and to AND gate 79. The OR gate 81 in turn produces a high output to turn on the fast oscillator 35. Because the up/down input to the phase timer 50 is again low, the phase timer counts down. When the phase timer count reaches zero, a high output signal is driven out of the phase timer 50 to AND gate 79, causing AND gate 79 to produce a high OUTPUT signal. The high OUTPUT signal produces the pulse position modulated response to the external device which is independent of the phase uncertainty.

Figure 7:
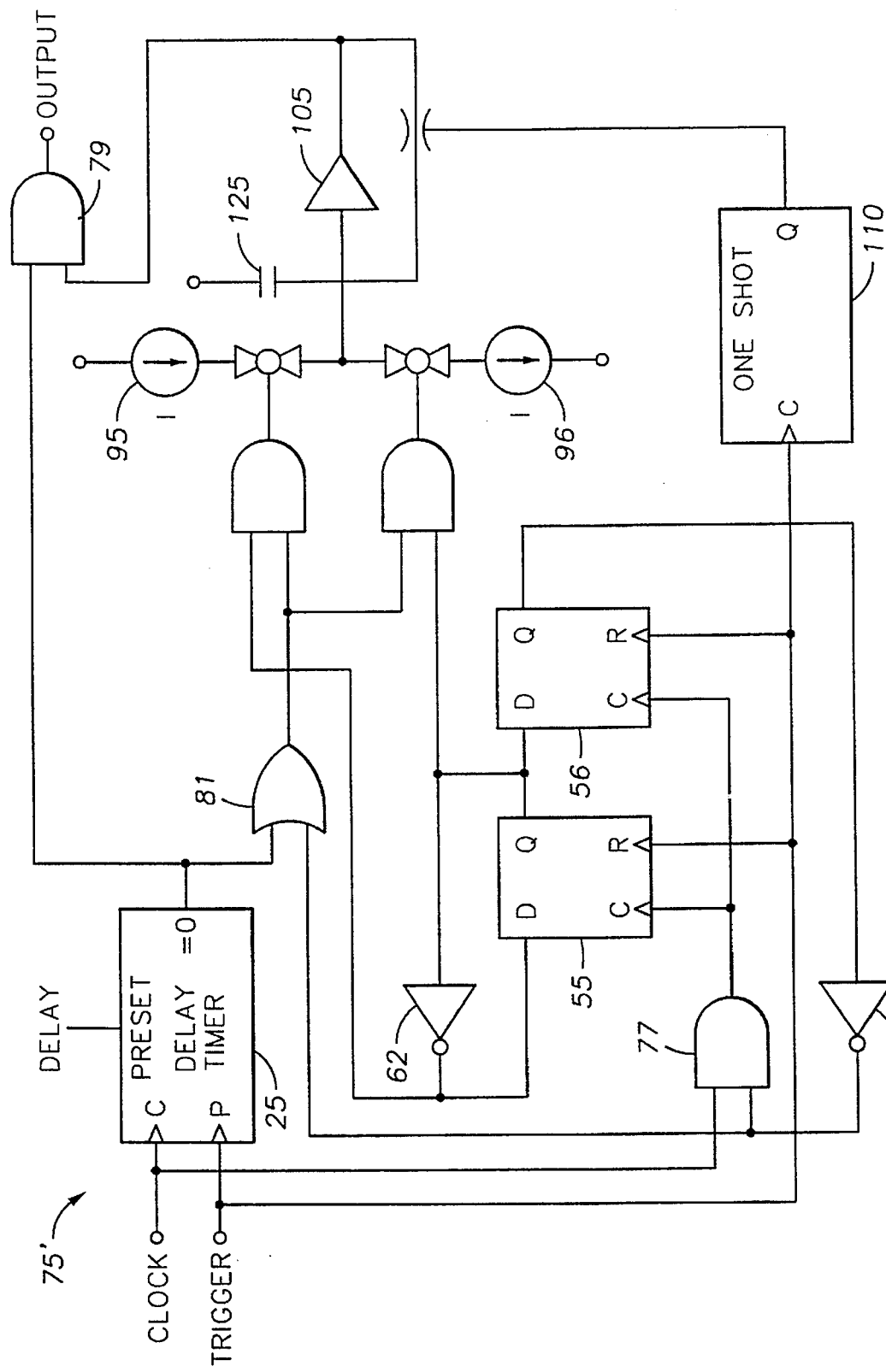
FIG. 7 is a schematic drawing depicting an alternative construction of a timing generator in accordance with the method of FIG. 3.

An alternative implementation for the timing generator is shown in FIG. 7. FIG. 7 incorporates an analog timing generator 75' for measuring phase uncertainty. FIG.7 is similar to FIG. 6 except that the phase timer is replaced with a capacitor 125, whose voltage represents the state variable. Two matching current sources 95, 96 are used to vary the voltage of capacitor 125 in either direction in accordance with the method of FIG. 3. A comparator 105 compares the voltage across capacitor 125 with a reference, such as 0 volts, and produces an output signal when the voltage on capacitor 125 crosses zero. In addition, a one shot multivibrator 110 is provided to short out capacitor 125 when the TRIGGER signal is received.

Both timing generator circuits 75 and 75' are meant to be illustrative of techniques for implementing the methodology of FIG. 3, and therefore should not be construed as limiting the method. Numerous other circuits and techniques, including software implementations, can be developed to achieve the same result.

Figure 4:
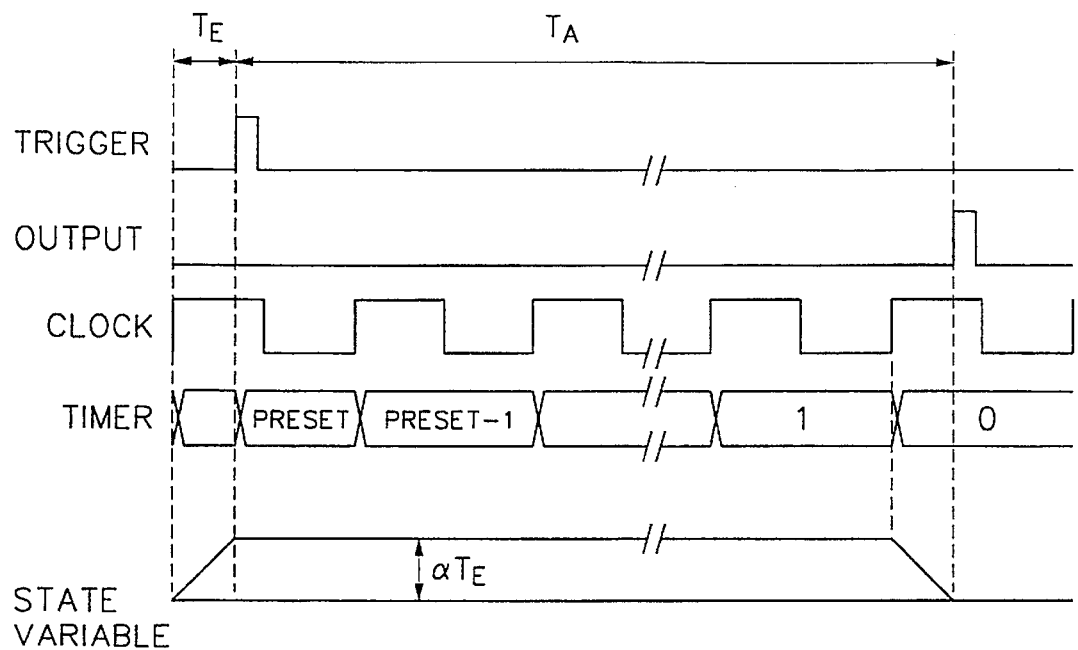
FIG. 4 shows a timing diagram illustrating the operation of an alternative embodiment of FIG. 3.

An alternative embodiment to the method of FIG. 3 is shown in FIG. 4. In FIG. 4, the state variable is initialized at the rising edge of each clock cycle and increased at a fixed rate. When a trigger event occurs, the state variable remains constant. When the delay timer or counter reaches zero, then the variable is decreased at the same rate to determine the additional delay period. One drawback of this method is that the circuit which varies the state variable must operate continuously in anticipation of a trigger event. As a result, this method would require more power consumption than the method shown in FIG. 3.

Figure 5:
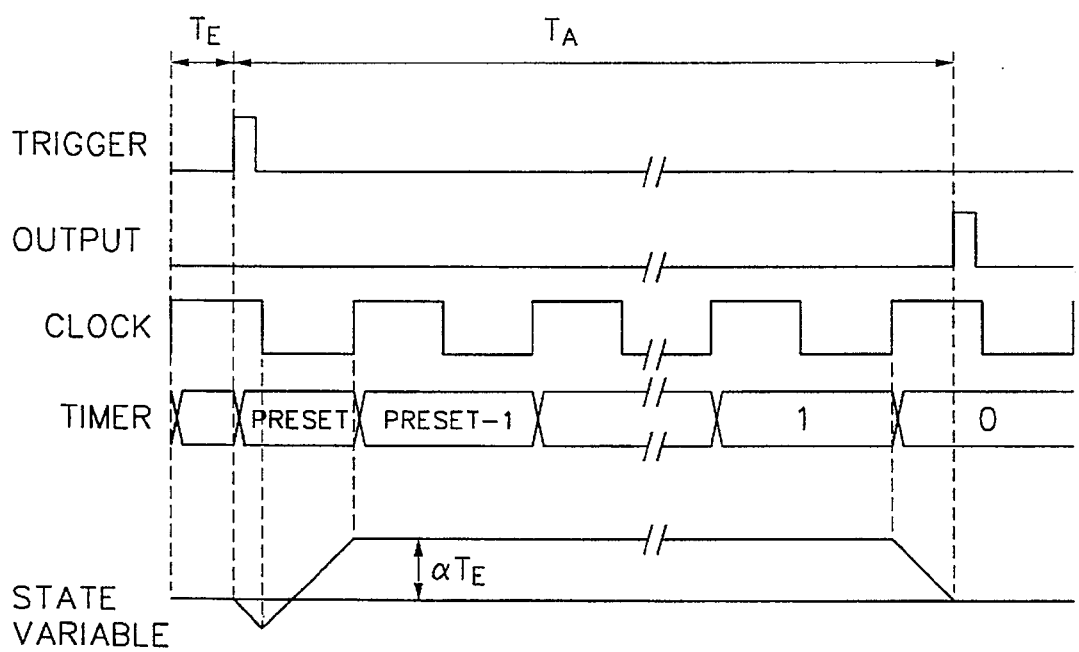
FIG. 5 shows a timing diagram illustrating yet another alternative embodiment of FIG. 3.

Referring now to FIG. 5, yet another method is shown in which the state variable circuit is sensitive to both the rising and falling edge of the system clock. Like FIG. 3, this method limits use of the state variable circuit to instances when the trigger event is detected. As shown in FIG. 5, the state variable is decreased after a trigger is detected until the first subsequent clock*edge (either rising or falling). At that time, the state variable is increased until the subsequent clock edge. This method permits the phase uncertainty $T_E$ to be measured in a shorter amount of time and thus reduces power consumption by permitting the state variable circuit to be powered down until the delay timer reaches zero. This variation, however, requires the clock cycle to have a duty cycle near 50% and the state of the clock when the trigger occurs must be known. The clock signal can be latched by the trigger event to provide this state information.

Figure 8:
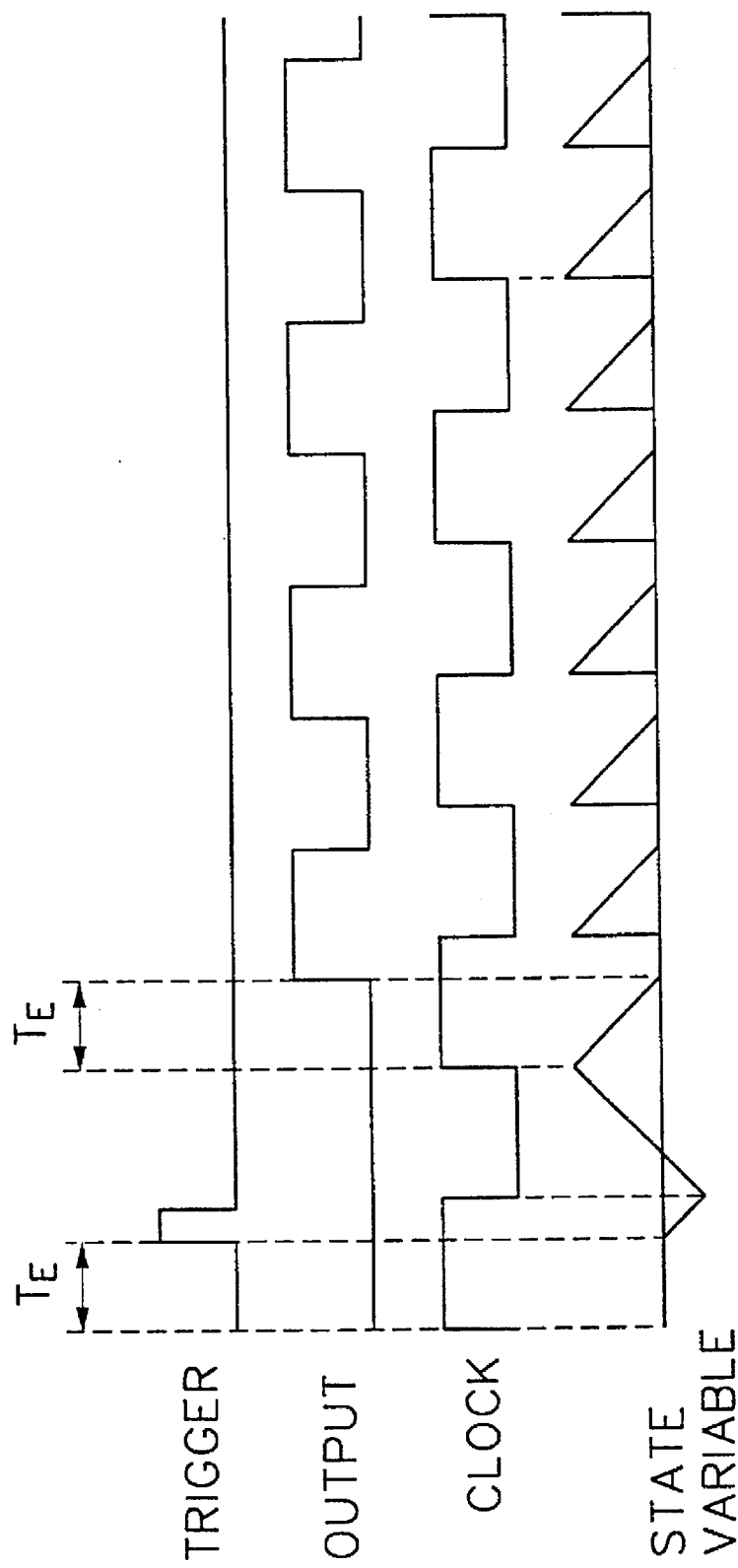
FIG. 8 is a timing diagram depicting a method for synchronizing an internal clock to an asynchronous event.

The present invention also can be used in situations other than performing pulse position modulation. For example, the present invention can be implemented in applications in which input signals arrive asynchronously with a system clock signal. For example, and as shown in FIG. 8, this technique can be used to produce a copy of the clock signal, which is synchronized with the trigger input signal. Operating a system in this fashion permits the use of a crystal oscillator for high accuracy while maintaining the ability to resynchronize the clock to each input event.

Referring still to FIG. 8, the phase uncertainty may preferably be measured as shown in FIG. 5. The resulting state variable value then is used to delay each edge of the clock signal, to produce an output clock which is synchronized with the trigger event. This adaptation requires that the state variable value be stored and reloaded on each clock edge. This output clock signal could then be used to drive any digital circuit which must operate synchronously with a trigger signal.

Figure 9:
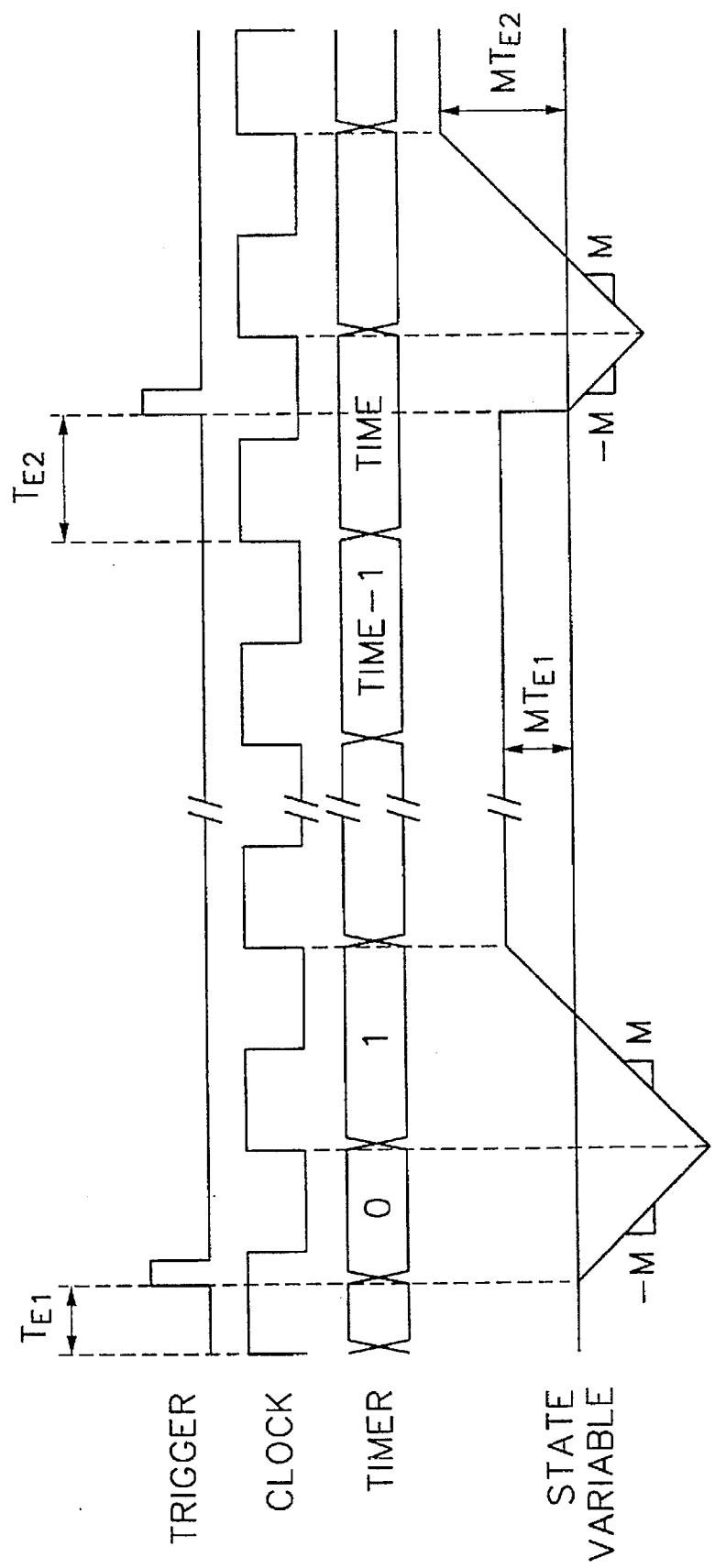
FIG. 9 is a timing diagram for measuring the time between the occurrence of two asynchronous events.

The techniques of the present invention also may be used to measure the time period between two asynchronous events, as shown in FIG. 9. This may be accomplished, as shown in FIG. 9, by performing the phase uncertainty measurement for each input event. Instead of using the resulting state variable value to produce a specific output response, however, the value can be stored and subtracted from the value obtained for the subsequent input event. The resulting difference, combined with the value obtained from a slower digital timer (such as a delay timer in FIG. 6), provides a relatively accurate measurement of the time between the two input events, as provided by:

$$\text{TIME} \mid \text{EVENTS} = \text{TIME} \times T_{CLK} + \frac{M(T_{E2} - T_{E1})}{M_E}$$

where TIME is the time given by the course digital timer;
$T_{CLK}$ is the period of the digital timer;
M is the actual slope of the state variable;
$M_E$ is the estimated slope of the state variable;
$T_{E2}$ is the phase uncertainty between event 2 and the internal clock; and
$T_{E1}$ is the phase uncertainty between event 1 and the internal clock.

If $M_E$ does not equal the actual slope M, the time obtained as the time between events will have some error. Because, however, the slow digital timer provides a course estimate of the actual time, the sensitivity of this error due to $M_E$ is reduced relative to alternative methods of measuring the time between asynchronous events.

While a preferred embodiment of the invention has been shown and described, modifications thereof can be made by one skilled in the art without departing from the spirit of the invention.

I claim:

1. A method for measuring phase difference between a trigger signal and an internal clock signal in an implantable device, said phase difference indicating the period of response of the implantable device after the trigger signal is received by the implantable device, said method comprising the steps of:

setting a state variable equal to an initial value;

changing the value of the state variable from the initial value at a first fixed rate after receiving the trigger signal;

changing the value of the state variable at a second fixed rate opposite in polarity to said first fixed rate when a first clock edge of said clock signal occurs subsequent to receiving the trigger signal;

beginning to count a preset period when said first clock edge occurs;

maintaining the value of the state variable when a second clock edge of said clock signal occurs;

completing the count of said preset period;

changing the value of the state variable at said first fixed rate after said count of said preset period is completed; and producing an output signal when said state variable returns to said initial value.

2. A method as in claim 1, wherein the first fixed rate is M and the second fixed rate is zero.

3. A method as in claim 2, wherein the value of the state variable is changed at a rate of −M after the count of the preset period is complete.

4. A method as in claim 1, wherein said first fixed rate has a slope −M, and said second fixed rate has a slope M, so that the first fixed rate has a slope that is the opposite of said second fixed rate.

5. A method as in claim 4, wherein said initial value is zero.

6. A method as in claim 5, wherein said first clock edge is a rising clock edge.

7. A method as in claim 6, wherein said second clock edge is a rising clock edge.

8. A method as in claim 7, wherein said count of said preset period only proceeds at rising clock edges of said clock signal.

9. A method as in claim 5 wherein said first clock edge is a falling clock edge.

10. A method as in claim 9, wherein said second clock edge is a rising clock edge.

11. A method for determining a period of response for an implantable medical device based upon a difference in phase between an external trigger signal and an internal clock signal in the implantable medical device, said method comprising the steps of:

storing a state variable with an initial value;

changing the value of the state variable at a first constant rate after detection of the trigger signal and until occurrence of a first clock edge of the internal clock signal;

loading a preset period into a counter upon detection of the external trigger signal;

changing the value of the state variable at a second fixed rate opposite in polarity to said first fixed rate after occurrence of the first clock edge;

initializing the counter to count the preset period after occurrence of said first clock edge;

maintaining the value of the state variable after occurrence of a second clock edge of said internal clock signal;

changing the value of the state variable at said first fixed rate after said count of said preset period is completed by said counter; and producing an output signal for the implantable device in response to the trigger signal when said state variable returns to said initial value.

12. A method as in claim 11, wherein said initial value is zero.

13. A method as in claim 11 wherein the end of said preset period defines a response synchronized with said trigger signal.

14. A method as in claim 11, wherein said first and second clock edges are different edge types.

15. A method as in claim 11, wherein said first and second clock edges are the same edge type.

16. A method as in claim 15, wherein the first and second clock edges are both rising clock edges.

17. A method as in claim 15, wherein the first and second clock edges are both falling clock edges.

* * * * *